US006689800B2

(12) United States Patent
Krzyaniak et al.

(10) Patent No.: US 6,689,800 B2
(45) Date of Patent: *Feb. 10, 2004

(54) β3-ADRENERGIC RECEPTOR AGONIST CRYSTAL FORMS, PROCESSES FOR THE PRODUCTION THEREOF, AND USES THEREOF

(75) Inventors: Joseph F. Krzyaniak, Pawcatuck, CT (US); Jennifer A. Lafontaine, San Diego, CA (US)

(73) Assignee: Pfizer Inc., New York, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 10/373,473

(22) Filed: Feb. 25, 2003

(65) Prior Publication Data
US 2003/0166686 A1 Sep. 4, 2003

Related U.S. Application Data
(60) Provisional application No. 60/360,248, filed on Feb. 27, 2002.

(51) Int. Cl.[7] .................. A61K 31/443; C07D 413/02
(52) U.S. Cl. .................................... 514/340; 546/271.4
(58) Field of Search ..................... 546/271.4; 514/340

(56) References Cited

U.S. PATENT DOCUMENTS

| | | | |
|---|---|---|---|
| 4,358,455 A | 11/1982 | Atkinson et al. | 424/263 |
| 4,478,849 A | 10/1984 | Ainsworth et al. | 424/285 |
| 4,918,091 A | 4/1990 | Cantello et al. | 514/369 |
| 5,019,578 A | 5/1991 | Fisher et al. | 514/275 |
| 5,030,640 A | 7/1991 | Fisher et al. | 514/339 |
| 5,051,423 A | 9/1991 | Lis et al. | 514/252 |
| 5,135,932 A | 8/1992 | Hauel et al. | 514/253 |
| 5,153,210 A | 10/1992 | Ainsworth et al. | 514/369 |
| 5,393,779 A | 2/1995 | Holloway et al. | 514/539 |
| 5,541,197 A | 7/1996 | Fisher et al. | 514/311 |
| 5,684,022 A | 11/1997 | Shuto et al. | 514/335 |
| 5,767,133 A | 6/1998 | Dow et al. | 514/339 |
| 5,776,983 A | 7/1998 | Washburn et al. | 514/605 |
| 5,840,738 A | 11/1998 | Bell et al. | 514/359 |
| 5,843,972 A | 12/1998 | Dow et al. | 514/367 |
| 5,859,044 A | 1/1999 | Dow et al. | 514/419 |
| 5,977,124 A | 11/1999 | Dow | 514/272 |
| 6,001,856 A | 12/1999 | Dow | 514/330 |
| 6,008,361 A | 12/1999 | Wright | 546/307 |
| 6,090,942 A | 7/2000 | DeVries et al. | 546/14 |
| 6,187,809 B1 | 2/2001 | Miyoshi et al. | 514/443 |
| 6,251,925 B1 | 6/2001 | Donaldson et al. | 514/354 |
| 6,265,581 B1 | 7/2001 | Bell et al. | 546/277.4 |
| 6,291,489 B1 | 9/2001 | DeVries et al. | 514/352 |
| 6,291,491 B1 | 9/2001 | Weber et al. | 514/357 |
| 6,441,181 B1 | 8/2002 | Scott | 546/276.4 |
| 6,451,587 B1 | 9/2002 | Burns et al. | 435/280 |
| 6,465,501 B2 | 10/2002 | Malamas et al. | 514/376 |
| 6,566,377 B2 * | 5/2003 | Day et al. | 514/340 |

FOREIGN PATENT DOCUMENTS

| | | | |
|---|---|---|---|
| EP | 0236624 | 8/1993 | C07D/309/38 |
| EP | 0543662 | 9/1996 | C07C/217/22 |
| EP | 0764632 | 3/1997 | C07C/233/52 |
| EP | 0882707 | 12/1998 | C07C/311/37 |
| EP | 1236723 | 9/2002 | C07D/295/22 |
| WO | WO 9000548 | 1/1990 | C07D/223/58 |
| WO | WO 9804526 | 2/1998 | C07D/209/04 |
| WO | WO 9821184 | 5/1998 | C07D/213/75 |
| WO | WO 9942455 | 8/1999 | C07D/277/40 |
| WO | WO 9945006 | 9/1999 | C07D/413/14 |
| WO | WO 0040560 | 7/2000 | C07D/213/80 |
| WO | WO 0232897 | 4/2002 | C07D/417/14 |
| WO | WO 0248134 | 6/2002 | C07D/311/58 |

OTHER PUBLICATIONS

U.S. Application No. 10/373119 filed on Feb. 24, 2003 entitled "β3 Adrenergic Receptor Agonists".
U.S. Application No. 10/370793 filed on Feb. 20, 2003 entitled "Processes and Intermediates Useful in preparing B3–Adrenergic Receptor Agonists".
U.S. Application No. 10/373492 filed on Feb. 25, 2003 entitled "B3–Adrenergic Receptors Agonist Crystal Forms, Processes for the Production Thereof, and Uses Thereof".

* cited by examiner

*Primary Examiner*—Alan L. Rotman
*Assistant Examiner*—Janet L Coppins
(74) *Attorney, Agent, or Firm*—Peter C. Richardson; Gregg C. Benson; Arlene K. Musser

(57) ABSTRACT

The present invention provides the tosylate salt of (R)-2-(2-(4-oxazol-4-yl-phenoxy)-ethylamino)-1-pyridin-3-yl-ethanol, the monohydrate of such salt, processes useful in the preparation of such salt and such monohydrate, pharmaceutical compositions comprising such salt, or such monohydrate, methods of treating β$_3$-adrenergic receptor-mediated diseases, conditions, and disorders in a mammal using such salt, such monohydrate, or such pharmaceutical compositions; and methods of increasing the content of lean meat in edible animals using such salt, such monohydrate, or such pharmaceutical compositions.

9 Claims, No Drawings

β3-ADRENERGIC RECEPTOR AGONIST CRYSTAL FORMS, PROCESSES FOR THE PRODUCTION THEREOF, AND USES THEREOF

This application claims the benefit of U.S. Provisional Application No. 60/360,248 filed Feb. 27, 2002 and incorporated herein by reference in its entirety.

FIELD OF THE INVENTION

The present invention provides the tosylate salt, the monohydrate of such salt, and pharmaceutical compositions comprising such salt, or such monohydrate, of the $\beta_3$-adrenergic receptor agonist (R)-2-(2-(4-oxazol-4-yl-phenoxy)-ethylamino)-1-pyridin-3-yl-ethanol, which agonist is useful in treating, inter alia, hypoglycemia, and obesity, and for increasing the content of lean meat in edible animals.

BACKGROUND OF THE INVENTION

Diabetes mellitus is characterized by metabolic defects in the production and utilization of carbohydrates which result in the failure to maintain appropriate blood sugar levels. The results of these defects include, inter alia, elevated blood glucose or hyperglycemia. Research in the treatment of diabetes has centered on attempts to normalize fasting and postprandial blood glucose levels. Current treatments include administration of exogenous insulin, oral administration of drugs, and dietary therapies.

Two major forms of diabetes mellitus are recognized. Type 1 diabetes, or insulin-dependent diabetes mellitus (IDDM), is the result of an absolute deficiency of insulin, the hormone that regulates carbohydrate utilization. Type 2 diabetes, or non-insulin-dependent diabetes mellitus (NIDDM), often occurs with normal, or even elevated, levels of insulin and appears to be the result of the inability of tissues to respond appropriately to insulin. Most Type 2 diabetic patients are also obese.

The tosylate salt, the monohydrate of such salt, and the pharmaceutical compositions comprising such salt, or such monohydrate, of the present invention effectively lower blood glucose levels when administered orally to mammals with hyperglycemia or diabetes.

Obesity constitutes a major health risk that leads to mortality and incidence of Type 2 diabetes mellitus, hypertension, and dyslipidemia. In the United States, more than 50% of the adult population is overweight, and almost 25% of the population is considered to be obese. The incidence of obesity is increasing in the United States at a three-percent cumulative annual growth rate. While the vast majority of obesity occurs in the United States and Europe, the prevalence of obesity is also increasing in Japan. Furthermore, obesity is a devastating disease which can also wreak havoc on an individual's mental health and self-esteem, which can ultimately affect a person's ability to interact socially with others. Unfortunately, the precise etiology of obesity is complex and poorly understood, and societal stereotypes and presumptions regarding obesity only tend to exacerbate the psychological effects of the disease. Because of the impact of obesity on society in general, much effort has been expended in efforts to treat obesity, however, success in the long-term treatment and/or prevention thereof remains elusive.

The tosylate salt, the monohydrate of such salt, and the pharmaceutical compositions comprising such salt, or such monohydrate, of the present invention also reduce body weight or decrease weight gain when administered to a mammal. The ability of such salt, or such monohydrate, and such compositions to affect weight gain is due to activation of $\beta_3$-adrenergic receptors which stimulate the metabolism of adipose tissue.

β-Adrenergic agents have been generally classified into $\beta_1$, $\beta_2$, and $\beta_3$ receptor-specific subtypes. Agonists of β-receptors generally promote the activation of adenyl cyclase. Activation of $\beta_1$ receptors involves an increase in heart rate while activation of $\beta_2$ receptors induces smooth muscle tissue relaxation which produces a drop in blood pressure and the onset of skeletal muscle tremors. Activation of $\beta_3$ receptors is known to stimulate lipolysis (e.g., the breakdown of adipose tissue triglycerides into glycerol and fatty acids) and metabolic rate (energy expenditure), thereby promoting the loss of fat mass. Accordingly, compounds that stimulate $\beta_3$ receptors are useful as anti-obesity agents, and can be further used to increase the content of lean meat in edible animals. In addition, compounds that are $\beta_3$ receptor agonists have hypoglycemic activity, however, the precise mechanism of this effect is presently unknown.

Until recently, $\beta_3$-adrenergic receptors were thought to be found predominantly in adipose tissue, however, $\beta_3$ receptors are now known to be located in such diverse tissues as the intestine (J. Clin. Invest., 91, 344 (1993)), and the brain (Eur. J. Pharm., 219, 193 (1992)). Stimulation of $\beta_3$ receptors has also been demonstrated to induce relaxation of smooth muscle in the colon, trachea, and bronchi. See, for example, Life Sciences, 44, 1411 (1989), Br. J. Pharm., 112, 55 (1994), and Br. J. Pharmacol., 110, 1311 (1993). Furthermore, stimulation of $\beta_3$ receptors has also been found to induce relaxation of histamine-contracted guinea pig ileum. See, for example, J. Pharm. Exp. Ther., 260, 1, 192 (1992).

The $\beta_3$ receptor is also expressed in the human prostate (J. Clin. Invest., 91, 344 (1993)). Because stimulation of the $\beta_3$ receptor causes relaxation of smooth muscles that have been shown to express the $\beta_3$ receptor, i.e., intestinal smooth muscle, one of ordinary skill in the art would also predict relaxation of prostate smooth muscle. Therefore, $\beta_3$ agonists are useful in the treatment or prevention of prostate disease.

Commonly assigned U.S. Pat. No. 5,977,124 discloses certain $\beta_3$-adrenergic receptor agonists having utility in the treatment of, inter alia, hypoglycemia and obesity.

U.S. Pat. No. 5,776,983 discloses certain catecholamines useful as $\beta_3$ agonists.

U.S. Pat. No. 5,030,640 discloses certain α-heterocylic ethanolamino alkyl indoles, which are useful as growth promoters, bronchodilators, anti-depressants, and anti-obesity agents.

U.S. Pat. No. 5,019,578 discloses certain α-heterocyclic ethanolamines useful as growth promoters.

U.S. Pat. No. 4,478,849 discloses pharmaceutical compositions comprising certain ethanolamine derivatives and methods of using such compositions in the treatment of obesity and/or hyperglycemia.

U.S. Pat. No. 4,358,455 discloses certain heterocyclic compounds of the structural formula Het-CHOH—CH$_2$—NH-aralkyl, which compounds as useful for treating glaucoma and cardiovascular disease.

European Patent Application Publication No. 0 516 349, published Dec. 2, 1992, discloses certain 2-hydroxyphenethyl amines which possess anti-obesity, hypoglycemic, and related utilities.

U.S. Pat. No. 5,153,210 discloses certain heterocyclic compounds of the formula $R^0$—X—CH(OH)—CH$_2$N ($R^1$)—C($R^2$)($R^3$)—(CH$_2$)$_n$—Y—A—$R^4$—$R^5$ which compounds are useful as anti-obesity and anti-hyperglycaemic agents.

PCT International Patent Application Publication No. WO 99/65877, published Dec. 23, 1999, discloses heterocyclic compounds having the structural formula

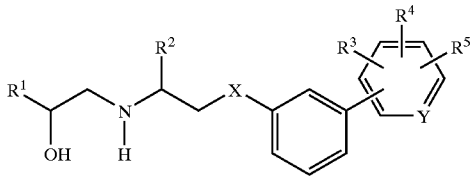

which compounds are useful for the treatment of disease susceptible to amelioration by the administration of an atypical β-adrenoceptor agonist.

Commonly assigned U.S. Provisional Application No. 60/242,274, filed Oct. 20, 2000, and incorporated herein by reference, discloses certain β$_3$-adrenergic receptor agonists of structural Formula (I),

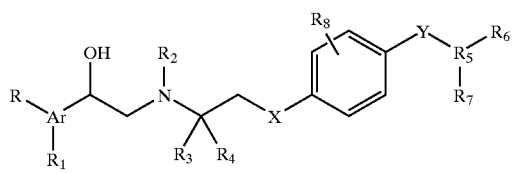

(I)

the stereoisomers and prodrugs thereof, and the pharmaceutically acceptable salts of the compounds, stereoisomers, and prodrugs, including the aforementioned (R)-2-(2-(4-oxazol-4-yl-phenoxy)-ethylamino)-1-pyridin-3-yl-ethanol.

The present invention provides the tosylate salt of (R)-2-(2-(4-oxazol-4-yl-phenoxy)-ethylamino)-1-pyridin-3-yl-ethanol, the monohydrate of such salt; processes useful in the preparation of such salt and such monohydrate; pharmaceutical compositions comprising such salt, or such monohydrate; methods of treating β$_3$-adrenergic receptor-mediated diseases, conditions, and disorders in a mammal using such salt, or such monohydrate, or such pharmaceutical compositions; and methods of increasing lean meat content in an edible animal using such salt, such monohydrate, or such pharmaceutical compositions.

SUMMARY OF THE INVENTION

The present invention provides the tosylate salt of (R)-2-(2-(4-oxazol-4-yl-phenoxy)-ethylamino)-1-pyridin-3-yl-ethanol; the monohydrate of such salt; processes useful in the preparation of such salt and such monohydrate; pharmaceutical compositions comprising such salt, or such monohydrate; methods of treating β$_3$-adrenergic receptor-mediated diseases, conditions, and disorders in a mammal using such salt, such monohydrate, or such pharmaceutical compositions; and methods of increasing the content of lean meat in edible animals using such salt, such monohydrate, or such pharmaceutical compositions.

DETAILED DESCRIPTION OF THE INVENTION

The present invention provides the tosylate salt of (R)-2-(2-(4-oxazol-4-yl-phenoxy)-ethylamino)-1-pyridin-3-yl-ethanol, the monohydrate of such salt; processes useful in the preparation of such salt and such monohydrate; pharmaceutical compositions comprising such salt, or such monohydrate; and methods of treating β$_3$-adrenergic receptor-mediated diseases, conditions, and disorders in a mammal using such salt, such monohydrate, or such pharmaceutical compositions. Such tosylate salt, such monohydrate, and such pharmaceutical compositions further possess utility for increasing the content of lean meat in edible animals, i.e., ungulate animals such as cattle, swine, and the like, as well as poultry.

As employed throughout the instant description and appendant claims, the term "therapeutically effective amount" means an amount of the tosylate salt, or the monohydrate of such salt, of (R)-2-(2-(4-oxazol-4-yl-phenoxy)-ethylamino)-1-pyridin-3-yl-ethanol, or a pharmaceutical composition comprising such salt, or such monohydrate, which attenuates, ameliorates, or prevents or delays the onset of one or more symptoms of a particular disease, condition, or disorder.

The term "mammal" means animals including, for example, dogs, cats cows, sheep, horses, and humans. Preferred mammals include humans, including members of both male and female sexes.

The term "pharmaceutically acceptable" indicates that the substance or composition must be compatible chemically and/or toxicologically with the other ingredients comprising a pharmaceutical formulation, and/or the mammal being treated therewith.

The terms "treat", "treating", or "treatment" embrace both preventative, i.e., prophyactic, and palliative treatment.

The compound (R)-2-(2-(4-oxazol-4-yl-phenoxy)-ethylamino)-1-pyridin-3-yl-ethanol may be prepared as disclosed in the aforementioned U.S. Provisional Application Serial No. 60/242,274. Alternatively, (R)-2-(2-(4-oxazol-4-yl-phenoxy)-ethylamino)-1-pyridin-3-yl-ethanol may also be prepared according to an exemplary process for preparing a compound of the structural formula

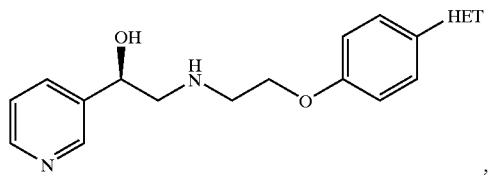

a pharmaceutically acceptable salt thereof, or a hydrate of the pharmaceutically acceptable salt, which process comprises the steps of:

(a) reducing an α-bromoketone derivative of the structural formula

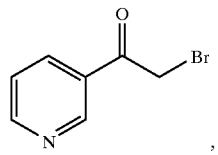

or an acid addition salt thereof, to form an (R)-bromoalcohol derivative of the structural formula

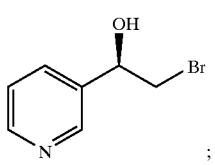

(b) protecting the (R)-bromoalcohol derivative of Step (a) to form an O-protected derivative of the structural formula

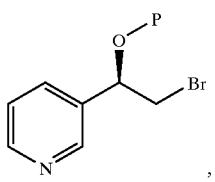

(c) condensing the O-protected derivative of Step (b) with an amine of the structural formula

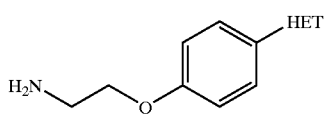

to produce an O-protected derivative of the structural formula

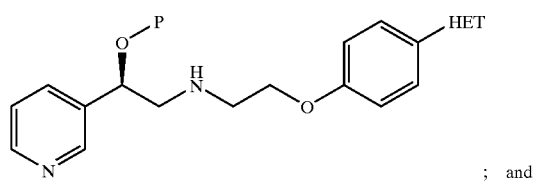

; and (d) deprotecting the O-protected derivative of Step (c) to form the compound of the structural formula

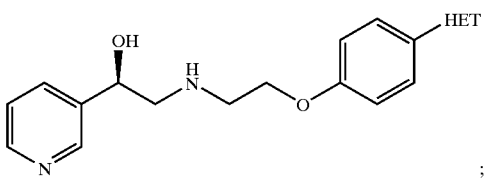

;

wherein:

HET is a heterocyclic moiety selected from the group consisting of oxazolyl, pyrazolyl, and thiazolyl; and P is an O-protecting moiety selected from the group consisting of —$SiR^1R^2R^3$, —$CH_2Ph$, —$CH_2(p-CH_3OPh)$, —$CH(OCH_2CH_3)CH_3$, and

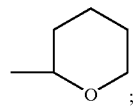

;

wherein $R^1$, $R^2$, and $R^3$ are, independently, ($C_1$–$C_6$)alkyl, or phenyl.

Preferably, P is —$SiR^1R^2R^3$, and HET is a heterocyclic moiety selected from the group consisting of 2-oxazolyl, 4-oxazolyl, 3-pyrazolyl, 4-pyrazolyl, 2-thiazolyl, and 4-thiazolyl. The process wherein P represents —$SiR^1R^2R^3$, wherein $R^1$ and $R^2$ are both —$CH_3$, and $R^3$ is —$C(CH_3)_3$ is especially preferred.

The stereospecific reduction step, denoted hereinabove as Step (a), preferably employs a fungal reducing agent. Generally, the use of fungal and/or microbial reducing agents in the stereospecific biotransformation of pharmaceutical intermediates is known. See, for example, R. N. Patel, Advances in Applied Microbiology, 43, 91–140 (1997). Specifically, the stereospecific reduction of α-haloketones with various microorganisms is also generally known. See, for example, R. N. Patel, et al., JAOCS, 75 (11), 1473–1482 (1998), which discloses the use of *Agrobacterium tumefaciens* ATCC 15955, *Alcaligenes eutrophus* ATCC 17697, *Arthrobacter petroleophagus* ATCC 21494, *Debaryomyces hansenii* ATCC 66354, *Mycobacterium* sp. ATCC 29676, *Rhodococcus rhodochorous* ATCC 14347, *Hansenula anomala* SC 13833, *H. anomala* ATCC 16142, *H. saturnus* SC 13829, and *Spingomonas paucimobilis* SC 16113 in the stereospecific reduction of α-bromoketones. The fungal reducing agent utilized in reduction Step (a) of the instant invention preferably comprises *Absidia cylindrospora* ATCC 22751 (American Type Culture Collection, Rockville, Md.). The aforementioned reduction step affords the corresponding (R)-bromoalcohol in a highly enantioselective yield, i.e. >90% enantiomeric excess. Preferably, the (R)-bromoalcohol so formed in the stereospecific reduction Step (a) is then isolated, either as a free base, or an acid addition salt thereof.

The (R)-bromoalcohol product formed in the stereospecific reduction Step (a) is then O-protected. Synthetic methods of protecting alcohol functional groups are well-known to one of ordinary skill in the art and may comprise, for example, functionalizing the alcohol as a silyl, ether, or ester derivative thereof. Although any conventional O-protecting group that is compatible with the reaction conditions employed in subsequent synthetic steps may be employed in the processes of the present invention, the (R)-bromoalcohol product of Step (a) is preferably protected as an O-silyl ether derivative. The preferred O-silylation step, generically denoted hereinabove as Step (b), may be effected according to standard methodologies that will be known to one of ordinary skill in the art. Such preferred O-silylation is typically effected by treatment of the (R)-bromoalcohol with an appropriately substituted silylating agent. Such silylating agents may comprise, for example, those silyl derivatives of the formula $R^1R^2R^3Si$—X, wherein X comprises an appropriate leaving group. Preferably, the silylating agent comprises a reactant of the formula $R^1R^2R^3Si$—X, wherein X is a leaving group selected from the group consisting of halogen (e.g., chloro or bromo), cyano, imidazolyl, triflate (trifluoromethanesulfonate), and the like. However, other silylating agents, that may be employed in accordance with the processes of the instant invention, will also be known to one of ordinary skill in the art. Preferably $R^1$, $R^2$, and $R^3$, within the definition of the protected alcohol moiety —$OSiR^1R^2R^3$ are, independently, ($C_1$–$C_6$)alkyl, or phenyl. The O-silyl ether derivative wherein $R^1$ and $R^2$ are both —$CH_3$, and $R^3$ is —$C(CH_3)_3$ is especially preferred.

Typically, such O-silylation is effected by condensing the alcohol to be protected with the silylating agent in the presence of a suitable organic base, for example, an alkylamine, such as triethylamine, N,N-diisopropylethylamine (Hunig's base), or a heterocyclic amine, such as imidazole or diazabicyclo[5.4.0]undec-7-ene (DBU), in a halogenated hydrocarbon solvent, such as dichloromethane. Alternatively, a polar, aprotic solvent, such as dimethylformamide or dimethylsulfoxide may also be employed. With respect to the O-silylation reaction of the present invention, dimethylformamide is preferred. Typically, such silylation is effected by stirring the reactants at, or about, room temperature for an extended period of time, i.e. overnight. However, such silylation may also be performed at greater, or lesser, than ambient temperature, where appropriate.

For a detailed discussion of methods of protecting alcohol functional groups, including those preferred methods employing silylating agents see, for example, T. W. Greene, et al., Protective Groups in Organic Synthesis, John Wiley & Sons, New York, N.Y. (1991), and the references cited therein.

The O-protected derivative so formed in Step (b) is then condensed in Step (c) with an amine of the structural formula

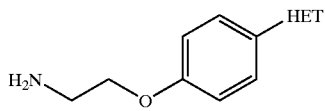

to provide a product of the structural formula

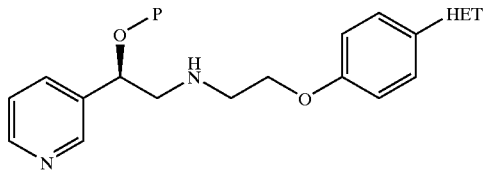

The aforementioned condensation Step (c) may be carried out under standard reaction conditions known to one of ordinary skill in the art. Preferably, the protected (R)-bromoalcohol and the amine are condensed in the presence of a suitable organic base, for example, an alkylamine, such as triethylamine, N,N-diisopropylethylamine (Hunig's base), in a polar, aprotic solvent, such as dimethylsulfoxide. Such condensation is typically effected at an elevated temperature, preferably in the general range of from about 40° to about 120° C. Preferably $R^1$, $R^2$, and $R^3$, within the definition of the preferred moiety —$SiR^1R^2R^3$ are, independently, ($C_1$–$C_6$)alkyl, or phenyl. The process where $R^1$ and $R^2$ are both —$CH_3$, and $R^3$ is —$C(CH_3)_3$ is especially preferred.

The amine compound utilized in Step (c) hereinabove may be prepared according to an exemplary process for preparing a compound of the structural formula

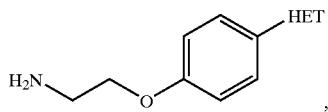

or an acid addition salt thereof, which process comprises the steps of:

(a') functionalizing a compound of the structural formula

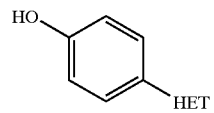

to provide a compound of the structural formula

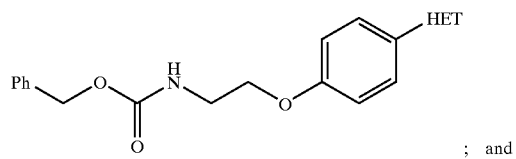 ; and (b') defunctionalizing the compound so formed in Step (a') to provide the compound of the structural formula

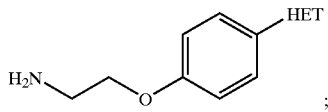 ;

wherein:
HET is a heterocyclic moiety selected from the group consisting of oxazolyl, pyrazolyl, and thiazolyl. Preferably, HET represents a heterocyclic moiety selected from the group consisting of 2-oxazolyl, 4-oxazolyl, 3-pyrazolyl, 4-pyrazolyl, 2-thiazolyl, and 4-thiazolyl.

In the functionalization step, denoted as Step (a') hereinabove, a phenolic compound of the structural formula

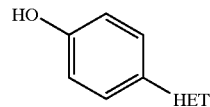

is functionalized to provide a carbamate of the structural formula

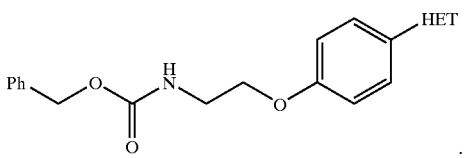

Such phenolic compounds, which may be prepared according to literature methods or, alternatively, according to the synthetic procedures disclosed hereinbelow, are most conveniently functionalized in Step (a') by the reaction thereof with a compound having the general formula $PhCH_2OCONHCH_2CH_2$—Y, wherein Y comprises an appropriate leaving group. Exemplary leaving groups comprise those selected from the group consisting of tosylate (p-toluenesulfonate), mesylate (methanesulfonate), halogen (e.g., bromo, chloro, or iodo), and the like. A mesylate leaving group is generally preferred. The compound of the general formula $PhCH_2OCONHCH_2CH_2$—Y, wherein Y is mesylate may be prepared as disclosed in C. A. Townsend, et al., Tetrahedron, 47, 2591 (1991). Functionalization of the phenolic compound is preferably effected in a polar, aprotic solvent, such as dimethylsulfoxide, in the presence of an inorganic base, for example, potassium carbonate. The functionalization is typically effected at an elevated temperature, generally in the general range of from about 40° to about 120° C.

The carbamate derivative so formed in functionalization Step (a') hereinabove is then defunctionalized in Step (b') to provide a compound of the structural formula

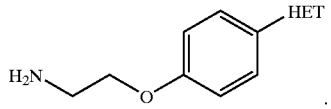

Such defunctionalization of the carbamate product formed in Step (a') may be carried out according to established methods. For example, the carbamate may be defunctionalized by catalytic hydrogenation employing a suitable metallic catalyst, such as a nickel salt, or a complex thereof, a palladium salt, or a complex thereof, or platinum, or a complex thereof. Preferably, the defunctionalization is effected in a polar, protic solvent, such as methanol, using ammonium formate and formic acid in the presence of a metallic catalyst, preferably, palladium on activated carbon. Such defunctionalization is normally performed at an elevated temperature, preferably at the reflux temperature of the solvent employed.

The amine product thus formed in Step (b') is then preferably isolated, either in the form of the free base, or in the form of an acid addition salt thereof. Conventional techniques of isolating such free base will be known to one of ordinary skill in the art. Likewise, the acid addition salt of the amine product may also be prepared according to known methods, for example, by treatment of the isolated free base with a conjugate organic acid, such as succinic, tartaric, acetic, citric, maleic, methanesulfonic, or p-toluenesulfonic acid, and the like, or a conjugate inorganic acid, such as hydrochloric, hydrobromic, sulfuric, or nitric acid, and the like. As was previously disclosed hereinabove, facile product isolation and augmented purity are normally satisfactorily achieved where such salt formation is carried out in a reaction-inert solvent, such as a non-solvent from which the desired salt precipitates upon formation, or in a solvent from which the formed salt precipitates upon subsequent addition of a non-solvent.

The deprotection step, denoted hereinabove as Step (d), may be performed according to standard methods that will be known to one of ordinary skill in the art. The preferred —O—SiR¹R²R³ derivative formed in Step (c) is preferably deprotected by the reaction thereof with a suitable alkylammonium fluoride, such as tetrabutylammonium fluoride. Such deprotection may be effected at ambient temperature in an aprotic solvent, for example, tetrahydrofuran. For a detailed discussion of methods of deprotecting O-silyl ethers see, for example, T. W. Greene, et al., supra, and the references cited therein.

The deprotected product of Step (d) is then preferably isolated, either in the form of the free base or, if desired, in the form of a pharmaceutically acceptable salt, or a hydrate of such pharmaceutically acceptable salt. Such isolation may be effected according to well-established methods. Likewise, the pharmaceutically acceptable salt may also be prepared according to known methods including, for example, treatment of the isolated free base with a conjugate organic acid, such as succinic, tartaric, acetic, citric, maleic, methanesulfonic, or p-toluenesulfonic acid, and the like. Alternatively, a conjugate inorganic acid, such as hydrochloric, hydrobromic, sulfuric, or nitric acid, and the like, may also be employed. The tosylate, i.e., p-toluenesulfonate, salt, abbreviated in the instant description and appendant claims as TsOH, of the deprotected product formed in Step (d) is especially preferred. For purposes of facilitating product isolation and augmenting purity, such salt formation is preferably carried out in a reaction-inert solvent, for example, a non-solvent from which the desired salt precipitates upon formation, or, more preferably, in a solvent from which the formed salt precipitates upon subsequent addition of a non-solvent.

One of ordinary skill in the art will further appreciate that pharmaceutically acceptable salts may form hydrated forms thereof, and such hydrated forms are embraced within the scope of the present invention. Hydrates of pharmaceutically acceptable salts may be prepared according to well-known methods including, for example, sublimation, crystallization of the hydrate from a single solvent, formation of the hydrate by evaporation from a binary mixture, vapor diffusion, thermal treatment, and the like. For a detailed discussion of methods of preparing hydrates of pharmaceutically acceptable salts see, for example, J. Keith Guillory, *Polymorphism in Pharmaceutical Solids*, Chapter 5, "Generation of Polymorphs, Hydrates, Solvates, and Amorphous Solids", pp. 183–219, Marcel Dekker, Inc. (1999). In the practice of the instant invention, the monohydrate of the tosylate salt of (R)-2-(2-(4-oxazol-4-yl-phenoxy)-ethylamino)-1-pyridin-3-yl-ethanol is preferred.

In one aspect, the invention provides the tosylate salt of (R)-2-(2-(4-oxazol-4-yl-phenoxy)-ethylamino)-1-pyridin-3-yl-ethanol, which salt is represented by the structural formula

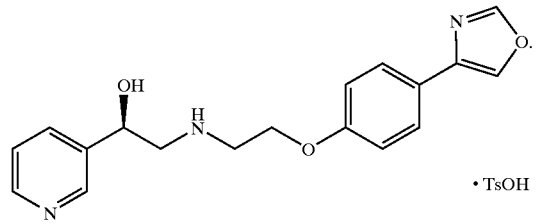

In another aspect, the invention provides the monohydrate of the tosylate salt of (R)-2-(2-(4-oxazol-4-yl-phenoxy)-ethylamino)-1-pyridin-3-yl-ethanol, which monohydrate is represented by the structural formula

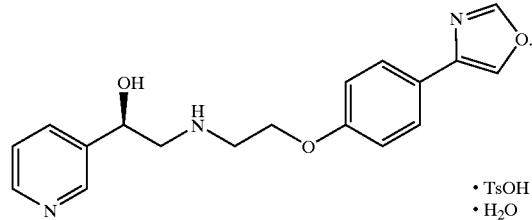

In yet another aspect, the instant invention further provides pharmaceutical compositions comprising the tosylate salt of (R)-2-(2-(4-oxazol-4-yl-phenoxy)-ethylamino)-1-pyridin-3-yl-ethanol, or the monohydrate of such salt; and a pharmaceutically acceptable carrier, vehicle, or diluent.

In yet another aspect, the invention further provides methods of treating $\beta_3$-adrenergic receptor-mediated diseases, conditions, or disorders in a mammal which comprise administering to a mammal in need of such treatment a therapeutically effective amount of the tosylate salt of (R)-2-(2-(4-oxazol-4-yl-phenoxy)-ethylamino)-1-pyridin-3-yl-ethanol, or the monohydrate of such salt; or a pharmaceutical composition comprising such salt, or such monohydrate. Preferably, the $\beta_3$-adrenergic receptor-mediated disease, condition, or disorder is selected from the group consisting of obesity, diabetes, irritable bowel syndrome, inflammatory bowel disease, esophagitis, duodenitis, Crohn's Disease, proctitis, asthma, intestinal motility disorder, ulcer, gastritis, hypercholesterolemia, cardiovascular disease, urinary incontinence, depression, prostate disease, dyslipidemia, and airway inflammatory disorder. The methods wherein the 3-adrenergic receptor-mediated diseases, conditions, or disorders are selected from the group consisting of obesity, diabetes, urinary incontinence, and irritable bowel syndrome are especially preferred.

The tosylate salt of (R)-2-(2-(4-oxazol-4-yl-phenoxy)-ethylamino)-1-pyridin-3-yl-ethanol, or the monohydrate of such salt, and the pharmaceutical compositions comprising such salt, or such monohydrate, further possess utility for increasing lean meat content in edible animals, i.e., ungulate animals such as cattle, swine, and the like, as well as poultry. Accordingly, the invention also provides methods of increasing lean meat content in an edible animal which comprise administering to the edible animal a lean meat increasing amount of the tosylate salt of (R)-2-(2-(4-oxazol-4-yl-phenoxy)-ethylamino)-1-pyridin-3-yl-ethanol, or the monohydrate of such salt; or a pharmaceutical composition comprising such salt, or such monohydrate.

The tosylate salt, or the monohydrate of such salt, of (R)-2-(2-(4-oxazol-4-yl-phenoxy)-ethylamino)-1-pyridin-3-yl-ethanol can be administered to a patient at dosage levels in the range of from about 0.01 to about 1,000 mg per day. For a normal adult human having a body mass of about 70 kg, a dosage in the range of from about 0.01 to about 300 mg is typically sufficient. However, some variability in the general dosage range may be required depending upon the age and weight of the subject being treated, the intended route of administration, and the like. The determination of dosage ranges and optimal dosages for a particular patient is well within the ability of one of ordinary skill in the art having benefit of the instant disclosure.

According to the methods of the invention, the tosylate salt, or the monohydrate of such salt, of (R)-2-(2-(4-oxazol-4-yl-phenoxy)-ethylamino)-1-pyridin-3-yl-ethanol is administered to a mammal in need of treatment therewith, preferably in the form of a pharmaceutical composition comprising a pharmaceutically acceptable carrier, vehicle, or diluent. Accordingly, such tosylate salt, or such monohydrate, can be administered to a mammal in any conventional oral, rectal, transdermal, parenteral, (e.g., intravenous, intramuscular, or subcutaneous), intracisternal, intravaginal, intraperitoneal, intravesical, local (e.g., powder, ointment, or drop), buccal, or nasal dosage form.

Compositions suitable for parenteral injection may comprise pharmaceutically acceptable sterile aqueous or nonaqueous solutions, dispersions, suspensions, or emulsions, and sterile powders for reconstitution into sterile injectable solutions or dispersions. Examples of suitable aqueous and nonaqueous carriers, diluents, solvents, or vehicles include water, ethanol, polyols (e.g., propylene glycol, polyethylene glycol, glycerol, and the like), suitable mixtures thereof, vegetable oils e.g., olive oil), and injectable organic esters such as ethyl oleate. Proper fluidity can be maintained, for example, by the use of a coating such as lecithin, by the maintenance of the required particle size in the case of dispersions, and by the use of surfactants.

These compositions may also contain adjuvants such as preserving, wetting, emulsifying, and dispersing agents. Prevention of microorganism contamination of these compositions can be effected with various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be effected by the use of agents capable of delaying absorption, for example, aluminum monostearate, and gelatin.

Solid dosage forms for oral administration include capsules, tablets, powders, and granules. In such dosage forms, the tosylate salt, or the monohydrate of such salt, of the invention is admixed with at least one inert customary pharmaceutical excipient (or carrier) such as sodium citrate, or dicalcium phosphate, or (a) fillers or extenders; (b) binders, as for example, carboxymethylcellulose, alginates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (e) solution retarders, as for example, paraffin; (f) absorption accelerators, as for example, cetyl alcohol and glycerol monostearate; (h) adsorbents, as for example, kaolin and bentonite; and/or (i) lubricants, as for example, talc, calcium stearate, magnesium stearate, solid polyethylene glycols, sodium lauryl sulfate, or mixtures thereof. In the case of capsules and tablets, the dosage forms may also comprise buffering agents.

Solid compositions of a similar type may also be employed as fillers in soft or hard filled gelatin capsules using such excipients as lactose or milk sugar, as well as high molecular weight polyethylene glycols, and the like.

Solid dosage forms such as tablets, dragees, capsules, and granules can be prepared with coatings and shells, such as enteric coatings and others well known in the art. They may also contain certain opacifying agents, and can be of such composition that they release the active compound or compounds in a delayed manner. Examples of embedding compositions that can also be employed are polymeric substances and waxes. The tosylate salt, or the monohydrate of such salt, of the instant invention can also be incorporated in micro-encapsulated form, if appropriate, with one or more of the above-mentioned excipients.

Liquid dosage forms for oral administration include pharmaceutically acceptable emulsions, solutions, suspensions, syrups, and elixirs. In addition to the tosylate salt, or the monohydrate of such salt, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oil, in particular, cottonseed oil, groundnut oil, corn germ oil, castor oil, and sesame seed oil, glycerol, tetrahydrofurfuryl alcohol, polyethylene glycols, and fatty acid esters of sorbitan, or mixtures of these substances, and the like.

Besides such inert diluents, the compositions may also comprise adjuvants, such as wetting agents, emulsifying and suspending agents, sweetening, flavoring, and perfuming agents.

Suspensions, in addition to the tosylate salt, or the monohydrate of such salt, may further comprise suspending agents, as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal or vaginal administration preferably comprise suppositories, which can be prepared by admixing the tosylate salt, or the monohydrate of such salt, of the invention with suitable non-irritating excipients or carriers such as cocoa butter, polyethylene glycol, or a suppository wax, which are solid at normal room temperature, but liquid at body temperature and, therefore, melt in the rectum or vaginal cavity thereby releasing such salt, or such monohydrate.

Dosage forms for topical administration may comprise ointments, powders, sprays, and inhalants. The tosylate salt, or the monohydrate of such salt, of the invention is admixed under sterile conditions with a pharmaceutically acceptable carrier, and any preservatives, buffers, or propellants that may also be required. Opthalmic formulations, eye ointments, powders, and solutions are also intended to be included within the scope of the present invention.

The following paragraphs describe exemplary formulations, dosages, etc. useful for non-human animals. In such animals, administration of the tosylate salt, or the monohydrate of such salt, of (R)-2-(2-(4-oxazol-4-yl-phenoxy)-ethylamino)-1-pyridin-3-yl-ethanol can be effected orally, or non-orally, for example, by injection.

An amount of the tosylate salt, or the monohydrate of such salt, of (R)-2-(2-(4-oxazol-4-yl-phenoxy)-ethylamino)-1-pyridin-3-yl-ethanol is administered such that an effective dose is received, generally a daily dose which, when administered orally to an animal, is usually between about 0.01 to about 1,000 mg per kg body mass, preferably between about 0.01 to about 300 mg per kg body mass.

Conveniently, the tosylate salt, or the monohydrate of such salt, can be carried in the drinking water such that a therapeutic dosage of the compound is ingested with the daily water supply. The salt can be metered directly into drinking water, preferably in the form of a liquid, water-soluble concentrate, such as an aqueous solution of the salt.

Conveniently, the tosylate salt, or the monohydrate of such salt, of the invention can also be added directly to the feed, as such, or in the form of an animal feed supplement, also referred to as a premix or concentrate. A premix or concentrate of the salt in a carrier is more commonly employed for the inclusion of the salt in the feed. Suitable carriers are liquid or solid, as desired, such as water, various meals such as alfalfa meal, soybean meal, cottonseed oil meal, linseed oil meal, corncob meal, molasses, urea, bone meal, and mineral mixes such as are employed commonly in poultry feeds. A particularly effective carrier is the respective animal feed itself; that is a small portion of such feed. The carrier facilitates uniform distribution of the tosylate salt, or the monohydrate of such salt, in the finished feed with which the premix is blended. It is important that such salt, or such hydrate, be thoroughly blended into the premix and, subsequently, the feed. In this respect, such salt, or such monohydrate, may be dispersed or dissolved in a suitable oily vehicle such as soybean oil, corn oil, cottonseed oil, and the like, or in a volatile organic solvent and then blended with the carrier. It will be appreciated that the proportions of such salt, or such monohydrate, in the concentrate are capable of wide variation since the amount(s) thereof in the finished feed may be adjusted by blending the appropriate proportion of premix with the feed to obtain a desired level of such salt, or such monohydrate.

High potency concentrates may be blended by the feed manufacturer with a proteinaceous carrier such as soybean oil meal and other meals, as described hereinabove, to produce concentrated supplements, which are suitable for direct feeding to animals. In such instances, the animals are permitted to consume the usual diet. Alternatively, such concentrated supplements may be added directly to the feed to produce a nutritionally balanced, finished feed containing a therapeutically effective amount or level of tosylate salt, or the monohydrate of such salt of the invention. The mixtures are thoroughly blended by standard procedures, such as in a twin shell blender, to ensure homogeniety.

If the supplement is used as a top dressing feed, it likewise helps to ensure uniformity of distribution of the tosylate salt, or the monohydrate of such salt, across the top of the dressed feed.

Drinking water and feed effective for increasing lean meat deposition and for increasing lean meat to fat ratio are generally prepared by mixing the tosylate salt, or the monohydrate of such salt, of (R)-2-(2-(4-oxazol-4-yl-phenoxy)-ethylamino)-1-pyridin-3-yl-ethanol with a sufficient amount of animal feed to provide from about $10^{-3}$ to about 500 ppm of such salt, or such monohydrate, in the feed or water.

The preferred medicated swine, cattle, sheep, and goat feed generally contain from about 1 to about 400 grams of the tosylate salt, or the monohydrate of such salt, per ton of feed, the optimum amount for these animals usually being about 50 to about 300 grams per ton of feed.

The preferred poultry and domestic pet feeds usually contain about 1 to about 400 grams and, preferably, about 10 to about 400 grams of the tosylate salt, or the monohydrate of such salt, per ton of feed.

For parenteral administration in animals, the tosylate salt, or the monohydrate of such salt, of the present invention may be prepared in the form of a paste or a pellet and administered as an implant, usually under the skin of the head or ear of the animal in which increase in lean meat deposition and improvement in lean meat to fat ratio is sought.

In general, parenteral administration involves injection of a sufficient amount of the tosylate salt, or the monohydrate of such salt, of the invention to provide the animal with about 0.01 to about 20 mg per kg body mass per day. The preferred dosage for poultry, swine, cattle, sheep, goats, and domestic pets is in the range of from about 0.05 to about 10 mg per kg body mass per day.

Paste formulations can be prepared by dispersing the tosylate salt, or the monohydrate of such salt, in a pharmaceutically acceptable oil, such as peanut oil, sesame seed oil, and the like.

Pellets containing an effective amount of the tosylate salt, or the monohydrate of such salt, of the present invention can be prepared by admixing such salt, or such monohydrate, with a diluent such as carbowax, carnuba wax, and the like, and a lubricant, such as magnesium or calcium stearate, can be added to improve the pelleting process.

It will be appreciated that more than one pellet may be administered to an animal to achieve the desired dosage level which will provide the increase in lean meat deposition and improvement in lean meat to fat ratio desired. Moreover, it has been determined that implants may also be made periodically during the animal treatment period in order to maintain the proper drug level in the animal's body.

The present invention has several advantageous veterinary features. For the pet owner or veterinarian who wishes to increase leanness and/or trim unwanted fat from pet animals, the instant invention provides methods by which this may be accomplished. For poultry and swine breeders, utilization of the methods of the present invention yields leaner animals which command higher sale prices from the meat industry.

EXAMPLES

The present invention is illustrated by the following Examples. It is to be understood, however, that the invention is not limited to the specific details of these examples as other variations thereof will be known or apparent in light of the instant disclosure to one of ordinary skill in the art.

Preparation of Intermediates

Preparation of Intermediate (R)-2-Bromo-1-pyridin-3-yl-ethanol (I-1):

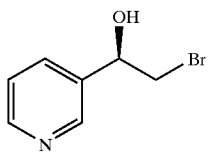

I-1

2-Bromo-1-pyridin-3-yl-ethanone hydrobromide (G. B. Davies, et al., *Aust. J. Chem.*, 42, 1735 (1989)) was contacted with cultures of *Absidia cylindrospora* ATCC 22751 grown in Fernbach flasks, or fermentor cultures containing medium A (40 g/l corn steep solids and 20 g/l glucose, adjusted to pH 4.85 prior to autoclaving). Fernbach flasks (8), each containing 500 ml of medium A, were inoculated with 5 ml of a seed culture of *Absidia cylindrospora* ATCC 22751. The seed cultures of *A. cylindrospora* were prepared in two 300 ml conical flasks, each containing 40 ml of medium A. These seed cultures were inoculated with a spore stock of *A. cylindrospora* and agitated (210 rpm) for about 24 hours at 29° C. After agitation for a total of about 41 hours at about 29° C., 25 ml of a 20 g/l aqueous solution of the hydrobromide salt of 2-bromo-1-pyridin-3-yl-ethanone was added to each of the Fernbach flask cultures. The flasks were agitated for about an additional 5 hours after which the contents of the flasks were combined and centrifuged to remove solid materials.

Two cultures of *Absidia cylindrospora* ATCC 22751 were grown in fermentors containing 8 l of medium A. The fermentors were each inoculated with a single culture of *A. cylindrospora* grown in Fernbach flasks containing 400 ml of medium A. The Fernbach flask cultures were inoculated with 1.8 ml of spore stock of *A. cylindrospora* ATCC 22751 and agitated (200 rpm) for about 40 hours at about 29° C. After about 24 hours, the two fermentor cultures were treated with an aqueous solution of 2-bromo-1-pyridin-3-yl-ethanone hydrobromide (30 g/l) which resulted in the addition of 8 g of 2-bromo-1-pyridin-3-yl-ethanone hydrobromide to one fermentor, and 16 g of 2-bromo-1-pyridin-3-yl-ethanone hydrobromide to the other fermentor. The fermentor culture that received 8 g of 2-bromo-1-pyridin-3-yl-ethanone hydrobromide was harvested about 24 hours following substrate addition, while the other fermentor was harvested about 5 hours following substrate addition. The contents of both fermentor cultures were centrifuged to remove solid materials.

The supernatant phases from the eight Fernbach flask cultures and the two fermentor cultures were combined, filtered through filter paper, and passed through a column containing 737 g of XAD-16® resin (Rohm & Haas; Philadelphia, Pa.). The resin was then eluted with mixtures of methanol and water (1 l 10% methanol, 1 l 20% methanol, 1 l 30% methanol, 1 l 50% methanol, 3×1 l 80% methanol, and 1 l 100% methanol) and fractions were collected. These fractions were analyzed by HPLC on a 4.6×150 mm Kromasil® C4 column (Phenomenex; Torrance, Calif.), eluting with 10 mM ammonium acetate:acetonitrile (76.5:23.5, v/v) at 1.0 ml/minute, and those fractions found to contain desired product (10% methanol-80% methanol) were pooled, concentrated to remove solvent, and extracted with ethyl acetate. The ethyl acetate extracts were combined, concentrated to about 600 ml, dried with magnesium sulfate, and filtered. This material was divided into several portions and then purified by flash chromatography on silica gel cartridges (1.2×7.5 cm and 4×15 cm, Biotage; Charlottesville, Va.) eluting with ethyl acetate and hexane mixtures containing 0.1% acetic acid(ethyl acetate:hexane:acetic acid; 60:40:0.1; v/v/v). Fractions containing desired product were concentrated to give 1.93 g (9.6%) of title compound as a light yellow oil, $\alpha_D=-16.4°$ (c=0.53, methanol). Chiral HPLC analysis of the product on 4.6×250 mm Chiralcel® OD column (Chiral Technologies; Exton, Pa.) eluting with hexanes:isopropyl alcohol (9:1, v/v) at 1.5 ml/minute revealed an enantiomeric excess of 91.2%.

$^1$HNMR (400 mHz, $d_6$-DMSO): δ 8.55 (d, 1H, J=2.1 Hz), 8.44 (dd, 1H, J=1.7, 4.6 Hz), 7.75 (dd, 1H, J=2.5, 4.2 Hz), 7.33 (m, 1H), 5.93 (d, 1H, J=4.6 Hz), 4.85 (m, 1H), 3.60 (ddd, 2H, J=5.0, 10.4, 14.9 Hz). GC-MS (m/z, %): 201/203 (M$^+$, 10), 108 (100).

Preparation of Intermediate (R)-3-(2-Bromo-1-(tert-butyl-dimethyl-silanyl)-ethyl)-pyridine (I-2):

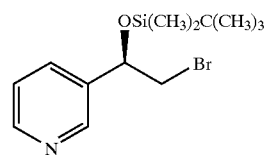

I-2

To a stirred solution of 1.54 g (7.61 mmol) of (R)-2-bromo-1-pyridin-3-yl-ethanol I-1 in 20 ml of dry N,N-dimethylformamide at room temperature was added 1.55 g (22.83 mmol) of imidazole followed by 1.72 g (11.4 mmol) of tert-butyldimethylsilyl chloride. The mixture was stirred at room temperature for about 18 hours and then an additional 1.55 g (22.83 mmol) of imidazole and 1.72 g (11.4 mmol) of tert-butyldimethylsilyl chloride were added, and the mixture was stirred at room temperature for about an additional 24 hours. The mixture was poured into 200 ml of water and extracted with ethyl acetate (2×200 ml). The organic extracts were combined, washed successively with water (1×40 ml), brine (1×40 ml), then dried over magnesium sulfate and concentrated in vacuo to furnish an oil. Chromatography on silica gel eluting with ethyl acetate:hexanes (2:3, v/v) provided 1.41 g (58% yield) of the desired title compound as a clear oil, $\alpha_D=-51.5°$ (c=0.60, chloroform). Chiral HPLC analysis of the product on 4.6× 250 mm Chiralcel® OD column (Chiral Technologies; Exton, Pa.) eluting with hexanes:isopropyl alcohol (7:3, v/v) at 1.0 ml/minute revealed an enantiomeric excess of 91.3%.

$^1$HNMR (400 mHz, CDCl$_3$): δ 8.58 (s, 1H), 8.55 (m, 1H), 7.70 (d, 1H), 7.30 (m, 1H), 4.90 (m, 1H), 3.46 (ddd, 2H, J=1,2, 7.1, 8.3 Hz), 0.87 (s, 9H), 0.11 (s, 3H). MS (m/z, %): 316/318 (M$^+$, 100).

Preparation of Intermediate [2-(4-Oxazol-4-yl-phenoxy)-ethyl]-carbamic acid benzyl ester (I-3):

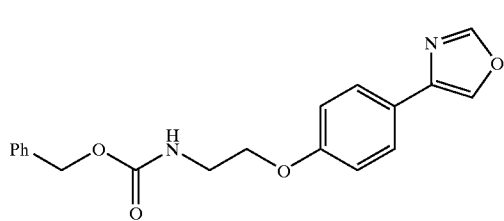

I-3

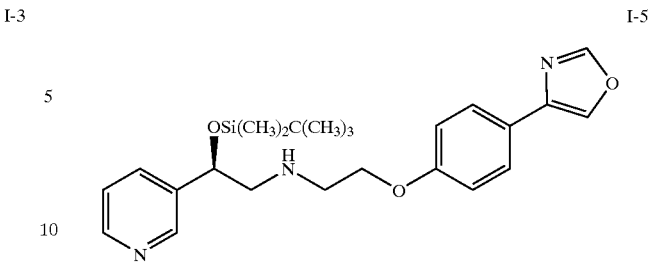

I-5

A stirred mixture of 290.0 g (1.80 mol) of 4-oxazol-4-yl-phenol (H. Jones, et al., *J. Med. Chem.,* 21, 1110 (1978)), 737.7 g (2.70 mol) of methanesulfonic acid 2-benzyloxycarbonylamino-ethyl ester, and 746.0 g (5.40 mol) of potassium carbonate in 4.6 l of dry dimethylsulfoxide was heated to about 85° C. An additional 500 ml of dimethylsulfoxide was added and the viscous slurry was stirred at about 80° C. for about an additional two hours. The resulting mixture was cooled to about 50° C., poured into about 1 l of stirred ice water, slurried for about one hour, and then filtered. The wet filter cake was washed with water (2×1 l), and then partially dried by aspiration under vacuum for about two hours. The moist solid was charged into a round-bottomed flask, 6 l of methanol was added, and the mixture was then warmed to about 60° C. where 3 l of water was added. The heating source was removed, the mixture was stirred for about eighteen hours, and then filtered. The filter cake was washed with 2:1 methanol/water (v/v; 2×500 ml), and then dried under vacuum at about 40° C. for about eighteen hours. The title compound (389.5 g, 64% yield) was obtained as a beige powder.

Preparation of Intermediate 2-(4-Oxazol-4-yl-phenoxy)-ethylamine (I-4):

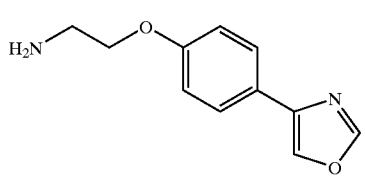

I-4

A stirred mixture of 234.0 g (0.692 mol) of [2-(4-oxazol-4-yl-phenoxy)-ethyl]-carbamic acid benzyl ester I-3, 295.1 ml (3.097 mol) of 1,4-cyclohexadiene, and 93.60 g of 10% Pd/C (50% water wet) in 5.6 l of methanol was stirred at room temperature for about twenty-two hours. The mixture was filtered through a pad of diatomaceous earth (13×3 cm), and the filter cake was then washed with 12 l of 100:1 v/v methanol/triethylamine. The filtrate was evaporated in vacuo, and to the residual solid was added 250 ml of toluene. The mixture was stirred at room temperature for about thirty minutes, 2.5 l of hexanes was then added over a period of about five to ten minutes, and the resulting slurry was then stirred for about one hour. The mixture was filtered, and the filter cake was then washed with a mixture of 1:10 toluene/hexanes (3×100 ml), and the solid was dried under vacuum at about 50° C. for about eighteen hours. The title compound (115 g, 81.5% yield) was obtained as a white powder.

Preparation of Intermediate (R)-(2-tert-Butyl-dimethylsilanoxy)-2-pyridin-3-yl-ethyl)-(2-(4-oxazol-4-yl-phenoxy)-ethyl)-amine (I-5):

A stirred mixture of 1.24 g (3.91 mmol) of (R)-3-(2-bromo-1-(tert-butyl-dimethyl-silanyl)-ethyl)-pyridine I-2, 1.6 g (7.83 mmol) of 2-(4-oxazol-4-yl-phenoxy)-ethylamine I-4, and 1.4 ml (7.83 mmol) of diisopropylethylamine in 20 ml of dry dimethylsulfoxide was heated at about 90° C. for about 18 hours. The mixture was poured into 400 ml of water and extracted with ethyl acetate (2×400 ml). The organic extracts were combined, washed successively with water (2×100 ml) and brine (1×100 ml), dried over magnesium sulfate, and concentrated in vacuo to furnish an oil. Chromatography on silica gel eluting with methanol:dichloromethane (1:19, v/v) yielded 963 mg (56% yield) of the title compound as an amber-colored oil, $\alpha_D$=−45.7° (c=0.49, chloroform).

$^1$HNMR (400 mHz, CDCl$_3$): δ 8.56 (d, 1H, J=2.1 Hz), 8.50 (dd, 1H, J=1.7, 5.0 Hz), 7.90 (d, 1H, J=0.8 Hz), 7.84 (d, 1H, J=0.8 Hz), 7.65 (m, 3H), 7.26 (m, 2H), 6.90 (m, 2H), 4.85 (dd, 1H, J=3.7, 8.3 Hz), 4.07 (m, 2H), 3.01 (dd, 2H, J=4.6, 6.2 Hz), 2.88 (dd, 2H, J=8.3, 12.0 Hz), 2.76 (dd, 2H, J=3.7, 11.6 Hz), 0.88 (s, 9H), 0.06 (s, 3H). MS (m/z, %): 441 (M$^+$+1, 100).

Preparation of Intermediate (R)-2-(2-(4-Oxazol-4-yl-phenoxy)-ethylamino)-1-pyridin-3-yl-ethanol (I-6):

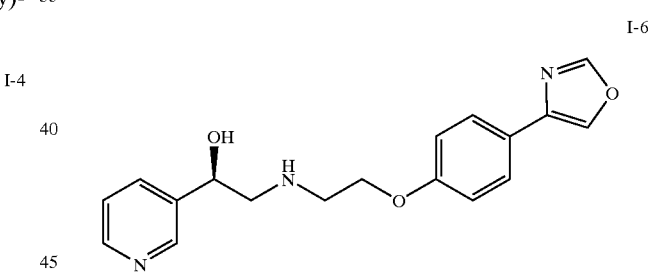

I-6

To a stirred solution of 646 mg (1.47 mmol) of (R)-(2-tert-butyl-dimethylsilanoxy)-2-pyridin-3-yl-ethyl)-(2-(4-oxazol-4-yl-phenoxy)-ethyl)-amine I-5 in 5 ml of dry tetrahydrofuran at room temperature was added 2.2 ml (2.20 mmol) of 1.0 M tetrabutylammonium fluoride in tetrahydrofuran. The mixture was stirred at room temperature overnight, poured into 100 ml of water, and extracted with ethyl acetate (2×100 ml). The organic extracts were combined, washed successively with water (1×20 ml) and brine (1×20 ml), dried over magnesium sulfate, and concentrated in vacuo to furnish a solid. Chromatography on silica gel eluting with methanol:dichloromethane (1:9, v/v) yielded a solid. Trituration with 10 ml of ethyl acetate:hexanes (1:1, v/v) afforded 250 mg (52% yield) of title compound as a white solid, m.p. 98–100° C., $\alpha_D$=−31.6° (c=0.58, chloroform). Chiral HPLC analysis of the product on 4.6×5 cm Chiralpak AS® column (Chiral Technologies; Exton, Pa.) eluting with acetonitrile:methanol (95:5, v/v) at 1.0 ml/minute revealed an enantiomeric excess of >99.9%.

$^1$HNMR (400 mHz, d$_6$-DMSO): δ 8.52 (d, 1H, J=2.1 Hz), 8.47 (d, 1H, J=0.8, 5.0 Hz), 8.41 (dd, 1H, J=1.7, 4.6 Hz), 8.38 (d, 1H, J=0.8 Hz), 7.70 (m, 3H), 7.30 (m, 1H), 6.96 (ddd, 2H, J=2.5, 4.6, 9.5 Hz), 5.47 (d, 1H, J=3.7 Hz), 4.67 (d, 1H), 4.02 (m, 2H), 2.89 (t, 2H, J=5.4 Hz), 2.72 (d, 2H, J=6.2 Hz). MS (m/z, %): 326 (M$^+$+1, 100).

Anal. Calc'd. for $C_{18}H_{19}N_3O_3$: C, 66.45; H, 5.89; N, 12.91. Found: C, 66.22; H, 5.92; N, 12.83.

Example 1

Preparation of (R)-2-(2-(4-Oxazol-4-yl-phenoxy)-ethylamino)-1-pyridin-3-yl-ethanol), ρ-toluenesulfonate salt:

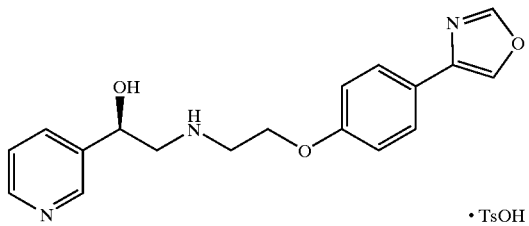

To a stirred solution of 197 mg (0.61 mmol) of (R)-2-(2-(4-oxazol-4-yl-phenoxy)-ethylamino)-1-pyridin-3-yl-ethanol) 1-6 in 2 ml of methanol at room temperature was added 118 mg (0.61) of ρ-toluenesulfonic acid monohydrate. The mixture was stirred at room temperature for about 30 minutes, and then 4 ml of isopropyl ether was added dropwise. The resulting precipitate was stirred for about an additional 15 minutes, filtered, washed with 4 ml of isopropyl ether:methanol (3:1, v/v), and dried to give 225 mg (74% yield) of the title compound as a white solid, m.p. 155.5° C., $α_D$=−16.9° (c=0.49, methanol). Chiral HPLC analysis on a 4.6 mm×5 cm Chiralpak AS® column (Chiral Technologies, Exton, Pa.) eluting with acetontrile:methanol (95:5, v/v) at 1.0 ml/minute revealed an enantiomeric excess of >99.9%.

$^1$HNMR (400 mHz, $d_6$-DMSO): δ 8.85 (s, br, 2H), 8.59 (d, 1H, J=1.7 Hz), 8.51 (m, 2H), 8.40 (d,1H, J=0.8 Hz), 7.80 (ddd, 1H, J=1.7, 3.7, 7.9 Hz), 7.72 (ddd, 2H, J=2.9, 4.6, 9.6 Hz), 7.43 (m, 3H), 7.04 (m, 4H), 6.30 (d,1H, J=4.2 Hz), 5.01 (dd, br, 1H, J=3.3, 7.1 Hz), 4.28 (d, br, 2H, J=5.4 Hz), 3.31 (d, br, 1H, J=12.5 Hz), 3.16 (t, br, J=11.2 Hz), 2.25 (s, 3H); MS (m/z, %): 326 (M$^+$+1, 100).

Anal. Calc'd. for $C_{25}H_{27}N_3SO_6$: C, 60.35; H, 5.47; N, 8.45. Found: C, 60.26; H, 5.48; N, 8.38.

Example 2

Preparation of (R)-2-(2-(4-Oxazol-4-yl-phenoxy)-ethylamino)-1-pyridin-3-yl-ethanol), ρ-toluenesulfonate salt, monohydrate:

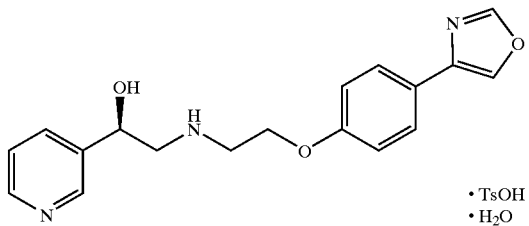

A 30 mg sample of (R)-2-(2-(4-oxazol-4-yl-phenoxy)-ethylamino)-1-pyridin-3-yl-ethanol), ρ-toluenesulfonate salt from Example 1 was pulverized to a particle size of less than about 10 μm, placed in a humidity chamber, and subjected to 100% relative humidity for about 14 days, where complete conversion of the anhydrous ρ-toluenesulfonate salt to the monohydrate was confirmed by near infrared spectroscopy.

Anal. Calc'd. for $C_{25}H_{29}N_3SO_7$: C, 58.2; H, 5.7; N, 8.1; S, 6.2. Found: C, 58.5; H, 5.6; N, 8.1; S, 6.6.

What is claimed is:

1. (R)-2-(2-(4-oxazol-4-yl-phenoxy)-ethylamino)-1-pyridin-3-yl-ethanol), p-toluenesulfonate salt.

2. (R)-2-(2-(4-oxazol-4-yl-phenoxy)-ethylamino)-1-pyridin-3-yl-ethanol), p-toluenesulfonate salt, monohydrate.

3. A pharmaceutical composition comprising (i) a therapeutically effective amount of (R)-2-(2-(4-oxazol-4-yl-phenoxy)-ethylamino) -1-pyridin-3-yl-ethanol), p-toluenesulfonate salt; and.

(ii) a pharmaceutically acceptable carrier, vehicle, or diluent.

4. A pharmaceutical composition comprising (i) a therapeutically effective amount of (R)-2-(2-(4-oxazol-4-yl-phenoxy)-ethylamino) -1-pyridin-3-yl-ethanol), p-toluenesulfonate salt, monohydrate; and (ii) a pharmaceutically acceptable carrier, vehicle, or diluent.

5. A method of treating a $β_3$-adrenergic receptor-mediated disease, condition, or disorder comprising the step of administering to a mammal in need of such treatment a therapeutically effective amount of (R)-2-(2-(4-oxazol-4-yl-phenoxy)-ethylamino)-1-pyridin-3-yl-ethanol), p-toluenesulfonate salt; or (R)-2-(2-(4-oxazol-4-yl-phenoxy)-ethylamino) -1-pyridin-3-yl-ethanol), p-toluenesulfonate salt, monohydrate.

6. A method of treating a $β_3$-adrenergic receptor-mediated disease, condition, or disorder comprising the step of administering to a mammal in need of such treatment a pharmaceutical composition comprising (i) a therapeutically effective amount of (R)-2-(2-(4-oxazol-4-yl-phenoxy)-ethylamino) -1-pyridin-3-yl-ethanol), p-toluenesulfonate salt; and (ii) a pharmaceutically acceptable carrier, vehicle, or diluent.

7. A method of treating a $β^3$-adrenergic receptor-mediated disease, condition, or disorder comprising the step of administering to a mammal in need of such treatment a pharmaceutical composition comprising (i) a therapeutically effective amount of (R)-2-(2-(4-oxazol-4-yl-phenoxy)-ethylamino) -1-pyridin-3-yl-ethanol), p-toluenesulfonate salt, monohydrate; and (ii) a pharmaceutically acceptable carrier, vehicle, or diluent.

8. The method of claim 5, 6 or 7 wherein said $β_3$-adrenergic receptor-mediated disease, condition, or disorder is selected from the group consisting of obesity, diabetes, irritable bowel syndrome, inflammatory bowel disease, esophagitis, duodenitis, Crohn's Disease, proctitis, asthma, intestinal motility disorder, ulcer, gastritis, hypercholesterolemia, cardiovascular disease, urinary incontinence, depression, prostate disease, dyslipidemia, and airway inflammatory disorder.

9. The method of claim 8 wherein said $β_3$-adrenergic receptor-mediated disease, condition, or disorder is selected from the group consisting of obesity, diabetes, urinary incontinence, and irritable bowel syndrome.

* * * * *